United States Patent
Kranbuehl et al.

(10) Patent No.: US 10,605,754 B2
(45) Date of Patent: Mar. 31, 2020

(54) DUCTILE-BRITTLE TRANSITION OF POLY(AMIDE) AS DETERMINED BY A HEAT OF FUSION-CRYSTALLINITY NUMBER

(71) Applicants: David E. Kranbuehl, Williamsburg, VA (US); John-Andrew S. Hocker, Newport News, VA (US)

(72) Inventors: David E. Kranbuehl, Williamsburg, VA (US); John-Andrew S. Hocker, Newport News, VA (US)

(*) Notice: Subject to any disclaimer, the term of this patent is extended or adjusted under 35 U.S.C. 154(b) by 279 days.

(21) Appl. No.: 15/828,651

(22) Filed: Dec. 1, 2017

(65) Prior Publication Data

US 2019/0170673 A1    Jun. 6, 2019

(51) Int. Cl.
| | |
|---|---|
| *G01N 25/00* | (2006.01) |
| *G01K 13/00* | (2006.01) |
| *G01N 25/48* | (2006.01) |
| *C08G 69/08* | (2006.01) |
| *C08L 77/02* | (2006.01) |
| *G01N 3/60* | (2006.01) |
| *G01N 3/18* | (2006.01) |
| *G01N 17/00* | (2006.01) |

(52) U.S. Cl.
CPC ........ *G01N 25/4866* (2013.01); *C08G 69/08* (2013.01); *C08L 77/02* (2013.01); *G01N 3/18* (2013.01); *G01N 3/60* (2013.01); *G01N 17/00* (2013.01); *G01N 2203/0226* (2013.01); *G01N 2203/0298* (2013.01)

(58) Field of Classification Search
USPC .......................................... 374/43, 16, 100
See application file for complete search history.

(56) References Cited

U.S. PATENT DOCUMENTS

| | | | |
|---|---|---|---|
| 5,614,683 A | 3/1997 | Kranbuehl | |
| 8,671,871 B2 * | 3/2014 | Huffman | G01K 3/04 116/207 |

* cited by examiner

*Primary Examiner* — Mirellys Jagan
(74) *Attorney, Agent, or Firm* — W & C IP

(57) ABSTRACT

The heat of fusion is used as a measure of the brittleness of a semicrystalline polyamide part. Parts made of or which include semicrystalline polyamides can be replaced or be identified for replacement when they are or will become brittle based on periodic heat of fusion measurements.

11 Claims, 3 Drawing Sheets

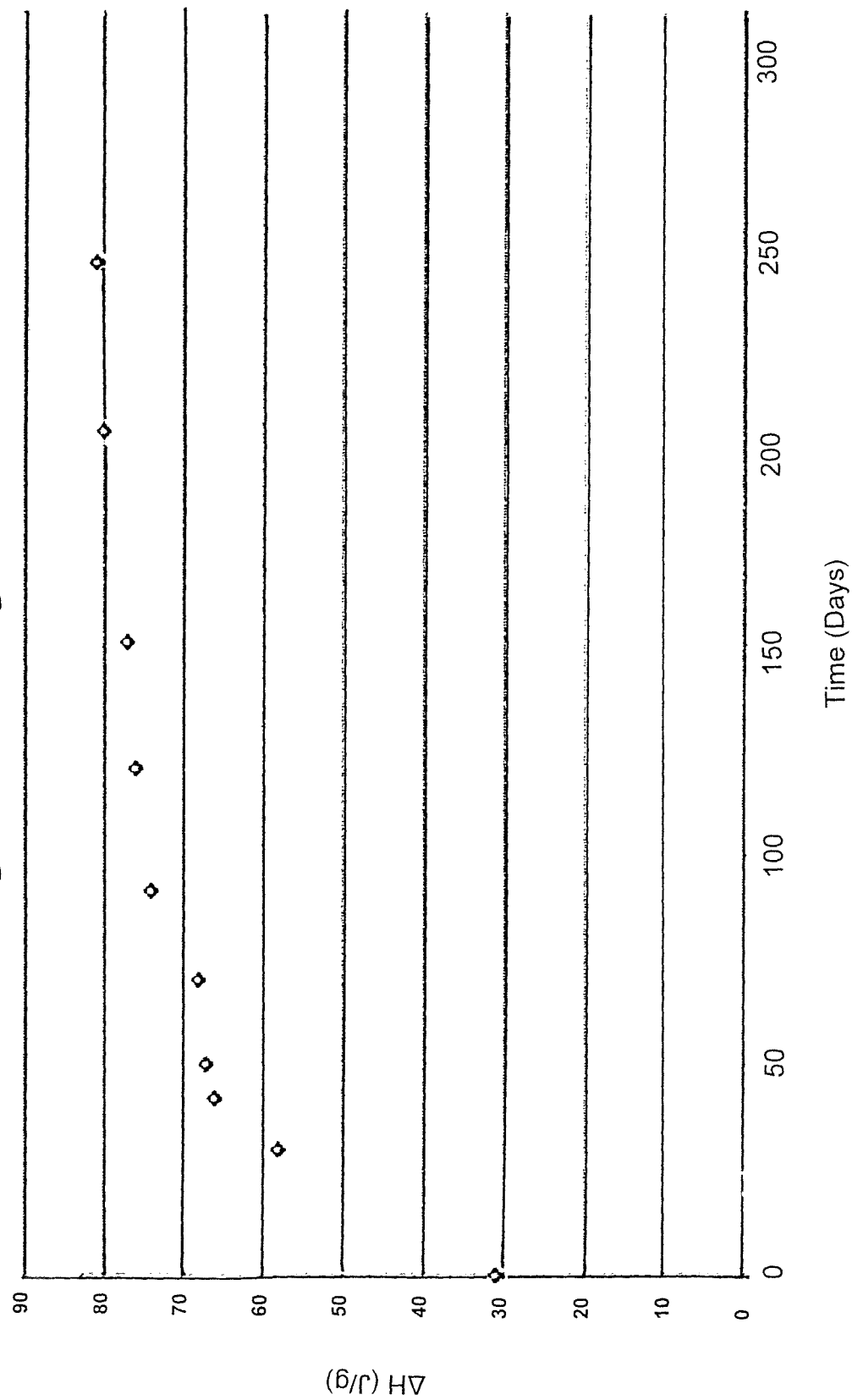

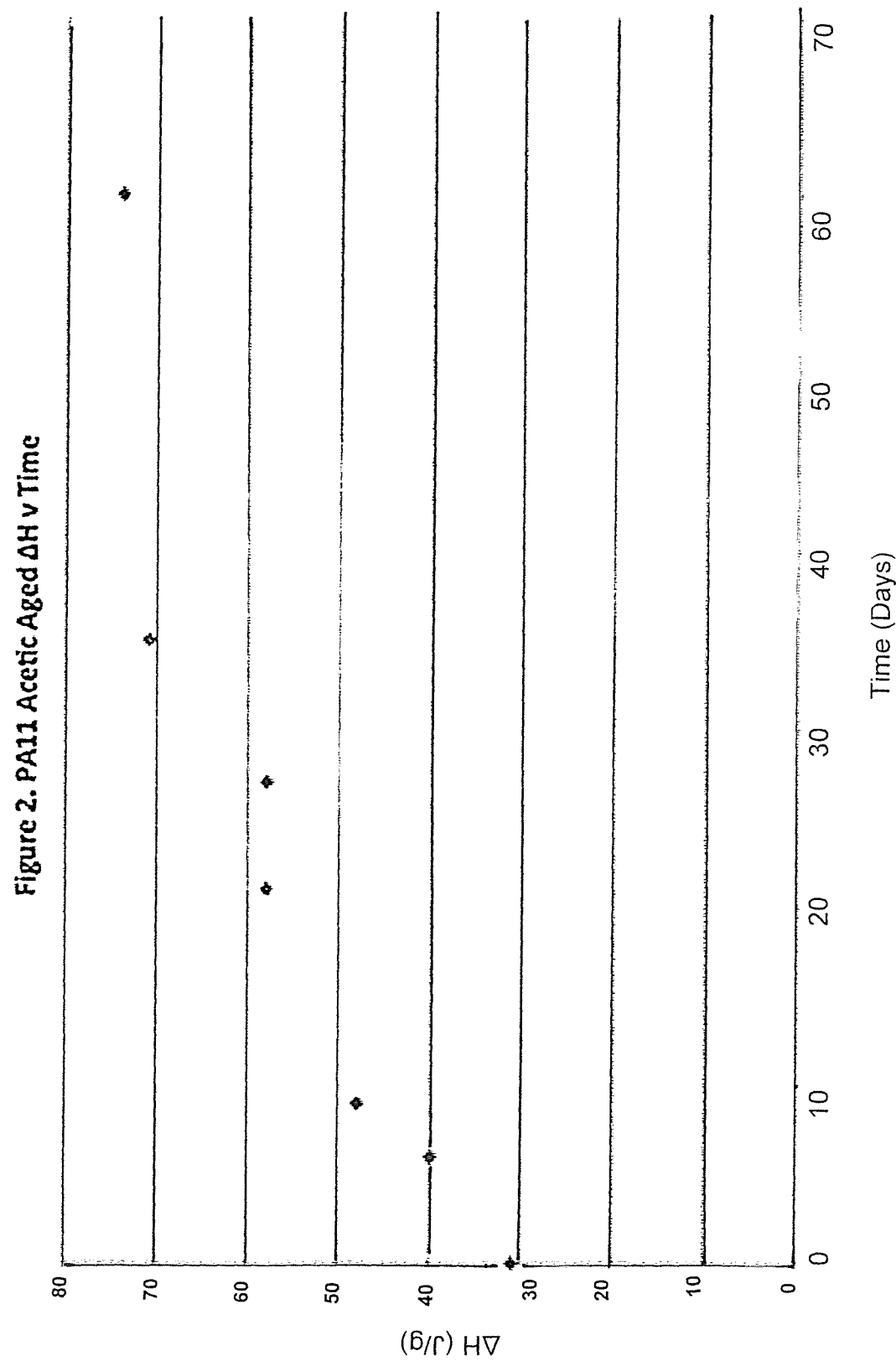

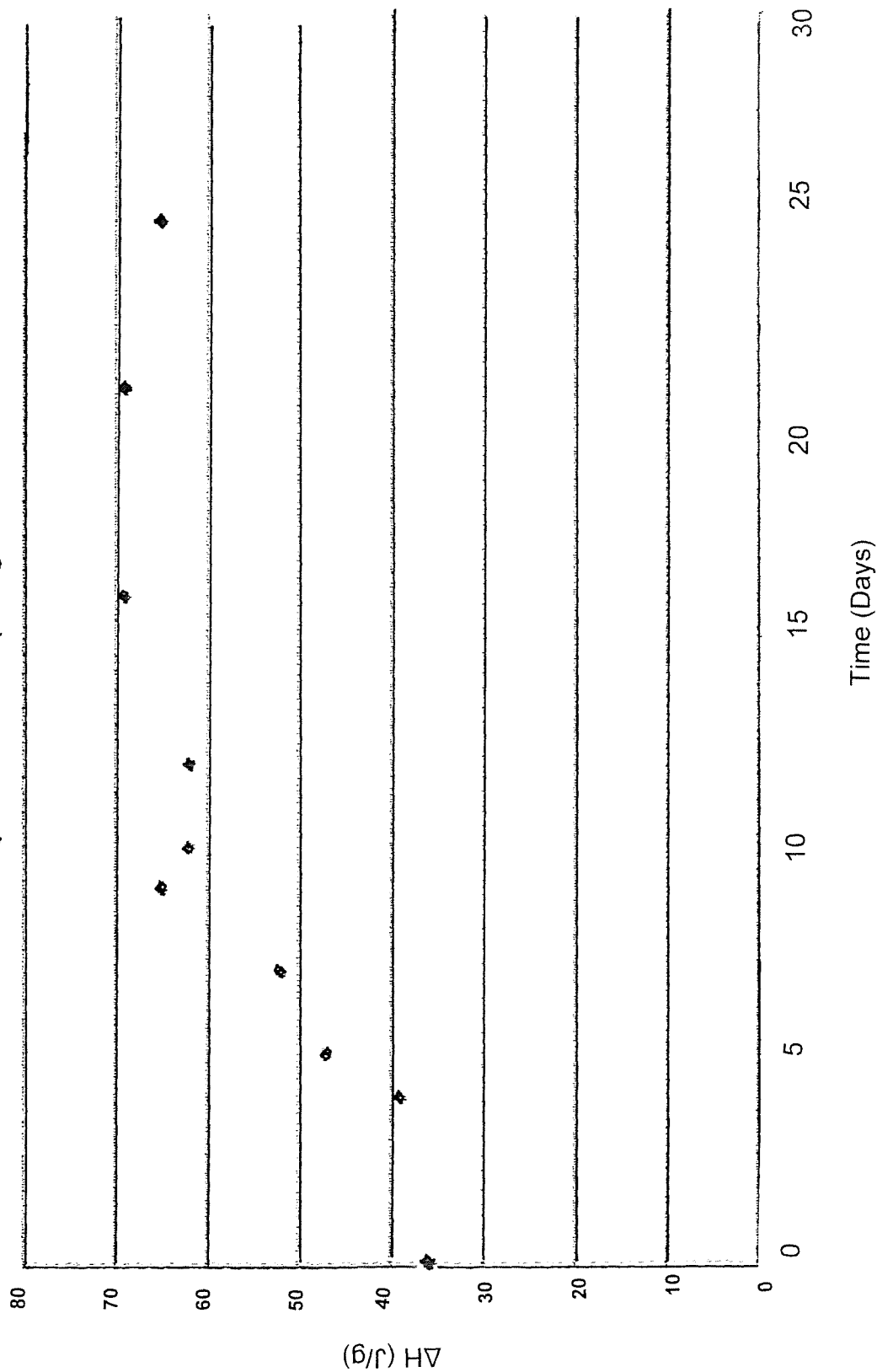

DUCTILE-BRITTLE TRANSITION OF POLY(AMIDE) AS DETERMINED BY A HEAT OF FUSION-CRYSTALLINITY NUMBER

BACKGROUND OF THE INVENTION

Field of the Invention

The present application generally relates to life monitoring of parts which are made from or which include polyamide materials and more particularly to using the Heat of Fusion-Crystallinity Number for evaluating the useful life remaining in a part comprised of polyamide.

Background Description

In U.S. Pat. No. 5,614,683 to Kranbuehl, it was determined that the average molecular weight was an important indicator of the life expectancy of a polyamide (PA) 11 (polyamide formed from 11-aminodecanoic acid). In particular, the patent demonstrated that average molecular weight measurements correlated with elongation measurements for the aged polyamide and that one could use molecular weight measurements to identify when polyamide parts needed to be replaced.

Life monitoring of plastic and composite parts continues to grow in importance in modern industrial processes. As plastic parts replace metal materials in load bearing structures as well as in extreme and corrosive environments, there is a continuing need for improved and accurate methods to ascertain when a part should be replaced. Replacing after a pre-set period of time runs the dual risks of (1) waiting too long to replace the part—i.e., in some situations the aging may occur earlier than the pre-set period, and (2) replacing the part too early—i.e. the part could have considerable life left even after the pre-set period expires which translates into an economic waste.

The heat of fusion is a number which is the amount of heat usually reported in joules per gram of a polymer which is needed to melt the crystalline region in polyamides, a semi-crystalline polymer. Here we report that the value of the heat of fusion is the physical property which determines when a polyamide becomes brittle. The ductile to brittle transition occurs over a short period of exposure time when a polyamide's elasticity rapidly drops from well over 200 percent to below 100 percent. This occurs during an exposure period during which the polyamide part is no longer safe for continued use in most applications. In these applications the part needs to have been replaced before it becomes brittle. The replacement criteria before the part becomes brittle represents the safety factor.

SUMMARY OF THE INVENTION

According to the present invention, the heat of fusion-crystallinity number for a part which consists of or is comprised of a polyamide is utilized for evaluating a number of properties including without limitation percent of life remaining, used up, and rate of aging of the part. The measurement can be made by periodically sampling a portion of the polyamide from a part being used in the field, and making the measurement. Alternatively, the measurement can be made by periodically sampling a portion of a witness coupon made from the polyamide which is in the field at a location adjacent to the part and which is exposed to the same environmental conditions as the part. An exemplary application of the invention would be to identify the life remaining, used up, and rate of aging of a polyamide liner used for transport of oil and gas. In some embodiments, the invention could be used for rating a life expectancy for a part by aging a sample of the polyamide in an environment which duplicates or simulates a field environment for the part or simulates accelerated aging environment for the part and making periodic measurements on the polyamide exposed to the environment.

U.S. Pat. No. 5,614,683 to Kranbuehl, the complete contents of which are herein incorporated by reference, teaches that an average molecular weight measurement such as by viscosity, size exclusion chromatography, multi-angle laser light scattering or combinations thereof can provide a person or automated system with information useful in determining whether it is time to replace a plastic part. This has been demonstrated over the past decade on polyamides used in deep sea flexible risers on offshore oil rigs. Fifteen years ago, in an effort to avoid devastating pipeline failures, the American Petroleum Institute studied and established the failure criteria of commercial PA11. In the API technical report 17ATR2, the safety factor failure criterion was determined to be a corrected inherent viscosity of 1.2 dL/g, which corresponds, based on our data and the Mark-Houwink relationship, to a mass average molecular weight of 35 kDa, and that PA11 approaches the ductile-brittle phase transition at that point.

Despite some prior success with the methodology taught in U.S. Pat. No. 5,614,683 to Kranbuehl, this invention demonstrates that the molecular weight method can be misleading and flawed. Molecular weight is not the key molecular measurement governing when a semi-crystalline plastic becomes brittle. Rather, it is shown herein that a measurement of the heat of fusion, the molecular parameter that measures extent of crystallization in the plastic, is the accurate and correct number to use to monitor the approach and the point-time at which a semi-crystalline plastic goes from elastic to brittle.

BRIEF DESCRIPTION OF THE DRAWINGS

FIGS. 1 to 3 are graphs plotting the heat of fusion versus time of exposure in the three ageing environments.

FIG. 1 plots the heat of fusion versus time of exposure in PA11 water aged ΔH v time.

FIG. 2 plots the heat of fusion versus time of exposure in PA11 acetic aged ΔH v time.

FIG. 3 plots the heat of fusion versus time of exposure in PA11 butyric aged ΔH v time.

DETAILED DESCRIPTION OF A PREFERRED EMBODIMENT OF THE INVENTION

Development of the Crystallinity Method

In an effort to understand the ductile-brittle transition region of polyamides, and using PA11 as model polyamide, we accelerated and monitored the aging of PA11 during degradation of the molecular weight in pH7 water and in water containing low molecular weight acids: acetic and butanoic acid. Organic acids are often found in crude at varying concentrations depending on the field. Organic acids in crude oil are known to increase the rate of molecular weight degradation. The mass average molecular weight (Mw) of the acid aged PA11 degraded four times faster in acetic acid and eight times faster in butanoic acid than the water aged PA11. With accelerated degradation, crystallinity increased more slowly than the change in molecular weight. This made it possible to separate the role of the increase in crystallinity from the decrease in molecular weight on when the polyamide becomes brittle. As a result, 20 kDa molecular weight PA11 when aged in the acid retained ductile behavior: greater than 200% ultimate strain during aging, while water aged PA11 at 35 kDa was brittle. In the aqueous pH7 conditions, the PA11 reaches the equilibrium molecular weight. As the PA11 hydrolysis progresses in water and the equilibrium molecular weight of 35 kDa is reached the embrittlement is controlled by the increases in crystallinity through thermal annealing. These aging measurements on acid aged and water aged PA11 show that a critical crystallinity, characterized by the heat of fusion of 66 J/g, determines the brittle phase transition independently of a given molecular weight.

This recent work shows that the determination of ductile brittle transition is more complex than previously thought. While the transition is determined by a combination of environmental factors, the fundamental molecular parameter that directly affects and accurately monitors ductility is the heat of fusion needed to melt the crystalline regions. Our work demonstrates ductility is not controlled by molecular weight as previously used but rather by the heat of fusion. Ductility can be retained at molecular values far below 35 to 40 kDa. By chance, under some aging environments the crystallinity happens to correlate with molecular weight change. This can happen at elevated accelerated aging temperatures in neutral water where the degradation environment which affects the molecular weight decrease in a similar manner as the increase in the heat of fusion needed to melt the crystalline regions.

EXPERIMENTAL

Two samples of commercial offshore grade PA11P40TLO Pellets, trade name Rilsan, manufactured by Arkema, were pressed in to films. These two film samples made at separate times and were identified as P1 and P2. P1 sample of PA11 contained N-n-Butylbenzenesulfonamide plasticizer at 12% by weight, a starting mass average molecular weight (Mw) of 100±10 kDa, a crystallinity content of 31 J/g, or 16% (based on the heat of fusion for pure crystalline PA11 is 189 J/g), and an ultimate strain of 500±50%. The P2 sample of PA-11 P40TLO, had 12 wt % N-n-Butylbenzenesulfonamide, a starting Mw of 80±5 kDa, a crystallinity of 35 J/g or 19%, and an ultimate strain of 370±30%. P1 was the thicker sample, 2±0.5 mm compared to sample P2, 0.3±0.02 mm. The differences in the properties of these two samples is due to the time and temperature conditions during formation of a film from the Arkema PA-11 P40TLO pellets.

Both P1 and P2 were formed into dogbone tensile test specimens and mechanical tests were performed on a MTS Systems Corporation instrumentat a rate of 6.35 mm/min.

The PA11 dogbones were immersed in deionized water, in acetic, or in butanoic acid solution at $6.3 \times 10^{-2}$ M and aged at 120° C. over a period of 4, 2, and 0.5 months, respectively, to accelerate aging and molecular weight degradation. Ace #40 high pressure rated glass tubes with Teflon plugs were used as containment vessels. Before sealing the pressure tube, oxygen was removed by sparging the aqueous solution with argon in-situ to achieve a concentration below 50 ppm.

A TA Instruments Q20 Differential Scanning calorimeter (DSC) was used to measure the heat of fusion-crystalline content of PA11. The ramp rate of 3° C./min was used to heat the samples under nitrogen from 40 to 220° C. with peak integration limits of 140 to 200° C.

To measure mass average molecular weight (Mw), we used multiple in-line size exclusion chromatography (SEC) columns (Shodex HFIP-LG, HFIP-805, and HFIP-803) with a Wyatt miniDAWN multi-angle laser light scattering (MALLS) detector and Wyatt Optilab 803 dynamic refractive index detector. The measured Mw values have a 6% error margin.

Results

Table 1 reports values of the measured molecular weight, heat of fusion, a calculated percent crystallinity based on a literature crystalline value of 189 J/g, and the percent elongation at break for each sample recovered from the aging environment and days aged in that environment. In Table 1, the water aged and the acetic aged PA-11 were samples made from P1, while the P2 material was aged in butanoic acid.

TABLE 1

| Day | Mw (kDa) Average | ΔH (J/g) Average | Crystallinity (%) | Ultimate Strain (%) |
|---|---|---|---|---|
| PA-11 P40 P1 Dogbone, Aged in DI Water, 120 C. | | | | |
| 0 | 110 | 31 | 5 | 573, 583, 665, 548 |
| 5 | 78 | 49 | 26 | 248 |
| 10 | 58 | 51 | 27 | 320 |
| 15 | 58 | 48 | 25 | 235 |
| 20 | 59 | 61 | 32 | 216 |
| 26 | 59 | 59 | 31 | 301 |
| 30 | 52 | 58 | 31 | 339 |
| 42 | 36 | 66 | 35 | 212 |
| 50 | 32 | 67 | 35 | 98 |
| 51 | 33 | 72 | 38 | 116 |
| 70 | 37 | 68 | 36 | 107 |
| 74 | 29 | 82 | 43 | 148 |
| 91 | 32 | 75 | 40 | 90 |
| 120 | 37 | 76 | 40 | 81 |
| 150 | 36 | 77 | 41 | 80 |
| 200 | 38 | 80 | 42 | 83 |
| 240 | 39 | 81 | 43 | 75 |
| PA-11 P40 P1 Dogbone, Aged in Acetic Acid, 120 C. | | | | |
| 0 | 110 | 31 | 5 | 573, 583, 665, 548 |
| 6 | 58 | 40 | 21 | 473 |
| 9 | 24 | 48 | 25 | 388 |
| 21 | 22 | 60 | 32 | 371 |
| 27 | 19 | 58 | 31 | 249 |
| 35 | 13 | 71 | 37 | 28 |
| 60 | 13 | 74 | 39 | 1 |
| PA-11 P40 P2 Dogbone, Aged in Butanoic Acid, 120 C. | | | | |
| 0 | 89 | 35 | 19 | 331, 355, 333, 388, 380, 359, 461, 413, 369, 357, 347, 404, 368, 345 |
| 4 | 32 | 39 | 21 | 258, 395, 312, 337, 393 |
| 5 | 30 | 47 | 25 | 294, 367, 336 |
| 7 | 26 | 54 | 28 | 304, 346, 316, 359 |
| 9 | 19 | 65 | 34 | 179, 180, 129 |
| 10 | 17 | 58 | 31 | 146, 147, 92 |
| 12 | 15 | 62 | 33 | 133, 117, 101 |
| 16 | 13 | 69 | 36 | 17, 20, 17 |
| 21 | 12 | 70 | 38, 35 | 9, 8, 9, 10, 11, 10 |
| 25 | 9 | 65 | 34 | 1 |

As the value of percent elongation from initial values 200% to 400% decreases, a percent elongation of 100% or below is an accepted value for being in the brittle transition. For aging in neutral water the first time the percent elongation falls below 100% occurs at a molecular weight of 36 kDa where the heat of fusion is 67 J/g. With increasing days the molecular weight remains constant, the heat of fusion increases and the percent elongation at break continues to decrease. For aging in acetic acid, the molecular weight decreases to 19 kDa with a good ductility of 249%. When the molecular weight decreases to 13 kDa the heat of fusion increases to 71 kDa and the percent elongation drops to 28%.

For the very rapid aging in butanoic acid, when the molecular weight decreases to 15 kDa, the heat of fusion 62 J/g and the percent elongation is just above 100%. When the molecular weight drops to 13 kDa and the heat of fusion drops to 69 J/g, the percent elongation drops below 100%.

Clearly, the heat of fusion is controlling ductility and is the fundamental molecular property to use to monitor the approach to the brittle state, the ductile to brittle transition, and the time for replacement.

There are many different types of polyamides, often referred to as nylons which differ by the number of carbons in the monomer unit such as PA-6, PA-11 and PA-12. Polyamides made from two monomers are represented by numbers of carbon atoms in each monomer such as PA-6/9, PA-6/10 and PA-6/12. Polyamides generally have additives such as in the P40TLO and in some cases a copolymer. This enhances the performance properties of the polyamide for a particular application or manufacturing process. Each polyamide will have its own heat of fusion value characterizing its ductile to brittle transition. The results above demonstrate that semicrystalline polyamides such as those with repeating structures of 25, 20, 15, 12, 11, 10, 9, 8, 7, 6, and 5 carbons in the monomer unit can be analyzed by measuring the heat of fusion to determine when parts made therefrom or which include such polyamides (be they homopolymers or copolymers) are approaching a brittle state. This will enable, for example, a technician or expert system to determine when a part should be replaced. Also, the rate of aging can be projected from making a plurality of heat of fusion measurements (e.g., two or more) at different time periods for the semicrystalline polyamide made or containing part.

In a simple embodiment of the invention, a threshold value of the heat of fusion is used to identify a time for part replacement. As can be seen from Table 1, the mechanical properties of the polyamide in the three different aging environments are deteriorating to a point where the polyamide's percent elongation drops well below 100 percent and the polyamide is brittle. The heat of fusion which is tracking the increase in the percent of crystallinity in the semi crystalline polyamide increases as the elongation at break decreases. This means the polymer, which is a combination of an amorphous component which is ductile and a rigid crystalline component which provides strength, becomes increasingly stiff with time in the aging environment. At the value of 65 J/g the polyamide becomes brittle and unsuitable for use in many applications such as for use in a flexible pipe used to transport crude from the ocean floor to a platform; the use for which PA-11 P40TLO additives are chosen. As previously used the changing molecular weight value provides no information of when the PA-11 becomes brittle.

FIGS. 1, 2 and 3 plot the heat of fusion versus time of exposure in the three aging environments. In operation of a part made from a polyamide such as an off shore PA-11 P40TLO flexible pipe, the heat of fusion would be periodically determined. In many applications a several mg piece of the polyamide part while in use may be retrieved. In other applications a small witness coupon located near the polyamide part and exposed to the same conditions of part may be periodically retrieved, a mg piece removed for analysis and the witness coupon returned. In other applications a series of witness coupons can be inserted in a spool located near the part and exposed to the aging environment. Here a witness coupon can be periodically removed and analyzed while a new fresh coupon can be inserted for later retrieval. It is important to note that the ductility of the part as determined by mg samples of the polymer allows one to determine the aged state of the part as a function of depth and position if one side is exposed and the other not. And while mechanical tensile test witness coupons could be used, this requires three or more large witness samples of dimensions 10 cm long by 1 cm wide or larger for one measurement of ductility. In almost all applications periodic measurement of change over time is not possible. Also it is clear from FIGS. 1, 2, and 3, that the change over time provides a means to determine the placement time for PA-11 P40TLO part in the particular crude coming from that well head environment. Furthermore, as shown in a plot such as in FIGS. 1,2, and 3, the operator can select their own replacement value for the heat of fusion where the safety factor is determined by the difference between the selected value and 65 J/g and the rate at which the heat of fusion value is changing.

While the invention has been described in terms of a single preferred embodiment, those skilled in the art will recognize that the invention can be practiced with modification within the spirit and scope of the appended claims.

The invention claimed is:

1. A method to analyze brittleness of a part which made of or contains a semicrystalline polyamide, comprising:
    obtaining one or more samples of the semicrystalline polyamide from the part or from a witness coupon made of the semicrystalline polyamide placed adjacent to the part and which is exposed to the same in use environment as the part; and
    detecting when a heat of fusion measurement of the one or more samples is at or above 65 J/g, wherein the part is determined to be brittle when the heat of fusion measurement is above 65 J/g.

2. The method of claim 1, wherein said semicrystalline polyamide includes aminoundecanoic acid.

3. The method of claim 1, wherein said obtaining and detecting steps are repeatedly performed multiple times over a selected time period.

4. The method of claim 1, wherein the obtaining step obtains said one or more samples from the part.

5. The method of claim 1, wherein the obtaining step obtains said one or more samples from the witness coupon.

6. A method to determine when a semicrystalline polyamide becomes brittle, comprising:
    aging the semicrystalline polyamide at a temperature and in an environment such that it becomes brittle over time while exposed to the aging environment;
    periodically removing samples of the semicrystalline polyamide from the aging environment;
    measuring a heat of fusion and a percent elongation at break for the samples; and
    determining brittleness for the semicrystalline polyamide to be a point where the heat of fusion for the samples corresponds to an elongation at break below 100 percent.

7. The method of claim 6, wherein the semicrystalline polyamide is a copolymer or homopolymer having a plurality of monomer repeats of 5 to 25 carbons.

8. The method of claim 6, wherein said polyamide includes aminoundecanoic acid.

9. A method to determine a time at which a semicrystalline polyamide is or will become brittle, comprising:

measuring a heat of fusion of the semicrystalline polyamide at a plurality different times, wherein the heat of fusion is measured on samples of the semicrystalline polyamide taken from in an in use environment which ages the semicrystalline polyamide;

determining a rate of change in the heat of fusion from a plurality of measurements measured in the measuring step; and estimating or identifying a time when the heat of fusion for the polyamide is or will be 65 J/g, wherein the time estimated or identified is the time when the semicrystalline polyamide is or will become brittle.

10. The method of claim 9, wherein the semicrystalline polyamide includes aminoundecanoic acid.

11. A method to determine when a semicrystalline polyamide is or will become brittle, comprising:

aging the semicrystalline polyamide at a temperature and in an environment such that it becomes brittle over time while exposed to the aging environment;

periodically removing samples of the semicrystalline polyamide from the aging environment;

measuring a heat of fusion and an elongation at break for the samples;

determining a rate of change in the heat of fusion from a plurality of measurements measured in the measuring step; and estimating or identifying, from the rate of change in the determining step, a time when the heat of fusion for the semicrystalline polyamide corresponds to an elongation at break below 100 percent, wherein the time estimated or identified is the time when the samples is or will become brittle.

* * * * *